United States Patent [19]

Sakai et al.

[11] Patent Number: 4,791,465
[45] Date of Patent: Dec. 13, 1988

[54] FIELD EFFECT TRANSISTOR TYPE SEMICONDUCTOR SENSOR AND METHOD OF MANUFACTURING THE SAME

[75] Inventors: Tadashi Sakai, Yokohama; Masaki Katsura, Yokosuka; Hideaki Hiraki, Kawasaki; Shigeki Uno, Tokyo; Masaru Shimbo, Yokohama; Kazuyoshi Furukawa, Kawasaki, all of Japan

[73] Assignee: Kabushiki Kaisha Toshiba, Kawasaki, Japan

[21] Appl. No.: 831,314

[22] Filed: Feb. 20, 1986

[30] Foreign Application Priority Data

Feb. 20, 1985 [JP] Japan .................................. 60-33101
Jun. 29, 1985 [JP] Japan ................................ 60-143790
Nov. 22, 1985 [JP] Japan ................................ 60-263016

[51] Int. Cl.[4] ........................................... H01L 29/66
[52] U.S. Cl. ....................................... 357/25; 357/55; 324/71.5
[58] Field of Search ....................... 357/25, 26, 28, 55, 357/23.1, 54; 324/71.5; 73/777

[56] References Cited

U.S. PATENT DOCUMENTS 4,400,869 8/1983 Wilner .................................... 357/26
4,671,846 6/1987 Shimbo ................................. 357/49

FOREIGN PATENT DOCUMENTS 59-33883 2/1984 Japan ..................................... 357/26

Primary Examiner—Andrew J. James
Assistant Examiner—Mark Prenty
Attorney, Agent, or Firm—Oblon, Fisher, Spivak, McClelland & Maier

[57] ABSTRACT

In a semiconductor sensor, the surfaces of first and second semiconductor substractes of a first conductivity type are made into flat surfaces by polishing the surfaces and are contacted each other so that the both substrates are bonded together. Source and claim regions are formed by diffusing an impurity of second conductivity type. The source and claim regions are separated through a through hole formed in the second substrate and are extended along the surface of the second substrate. An insulative layer is formed on the opposite surface of the second substrate and an inner surface of the through hole.

19 Claims, 9 Drawing Sheets

FIELD EFFECT TRANSISTOR TYPE SEMICONDUCTOR SENSOR AND METHOD OF MANUFACTURING THE SAME

BACKGROUND OF THE INVENTION

The present invention relates to a semiconductor sensor and, more particularly, to a field effect transistor type sensor for detecting a specific component in a solution.

A chemical sensor of field effect transistor (FET) type, i.e., ISFET (ion selective field effect transistor), comprises a silicon substrate, source and drain regions which are formed on the surface of the substrate, and an insulative film. A gate portion of the sensor is dipped in a solution so that a change in conductance between the source and drain regions, which corresponds to an ion concentration in the solution, is detected. In such a chemical sensor, since the gate portion is placed in direct contact with the solution, a contact surface thereof must be insulated. For this purpose, the device is coated with a gate insulative film (a silicon oxide film, or the like), and an insulative film acting as a protective film or a passivation film e.g., a silicon nitride film. Part of the insulative film is selectively etched to form a wiring layer connected to source and drain diffusion layers, and a metal deposition film or metal wiring is deposited on the etched portion, thus preparing a connecting portion for the external circuit.

Chemical sensors having structures shown in FIGS. 1A, 1B, 2A, 2B, and 3 have been known.

Figure 1A:
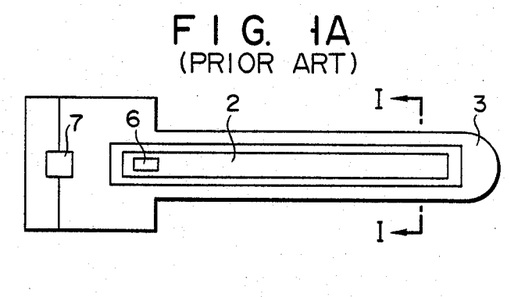
FIGS. 1A and 2A are plan views schematically showing conventional ISFETs.
Figure 1B:
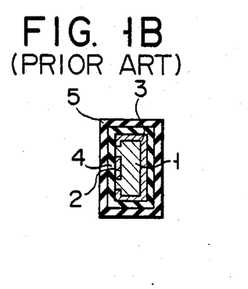
FIGS. 1B and 2B are sectional views taken along lines I—I and II—II of FIGS. 1A and 2A, respectively.

The sensor shown in FIGS. 1A and 1B has a probe-like shape. In the sensor shown in FIGS. 1A and 1B, $n^+$-type drain region 2 is formed on the surface of p-type silicon substrate 1, and $n^+$-type source region 3 is so formed on the surface of the substrate as to surround drain region 2. Silicon oxide film 4 and silicon nitride film 5, which respectively serve as a gate insulative film and a protective film, are deposited on the entire surface of silicon substrate 1. In this structure, a gate portion of the FET is defined by the source and drain regions at one side of substrate 1, a channel region therebetween, and the insulative film. Insulative film 4 on the other side of source and drain regions 2 and 3 is selectively etched, and metal films 6 and 7 serving as contact layers are formed thereon.

In the chemical sensor of this type, however, when part of silicon substrate 1 is exposed, current leakage occurs between elements in the solution. Because of this, insulative film 4 must be formed on the entire circumferential surface of substrate 1. Since wafers cannot be directly subjected to an insulative film forming process, chips having an outer shape like the sensor must be cut from the wafer, and thereafter, the insulative film must be formed on individual chips. For this reason, this conventional method is unsuitable for mass-production, and the chips are easily damaged during their manufacture. Even if a chip is not damaged during manufacture, the resultant sensor has a decrease in mechanical strength because it receives a liquid pressure on only one side of substrate 1.

Figure 2A:
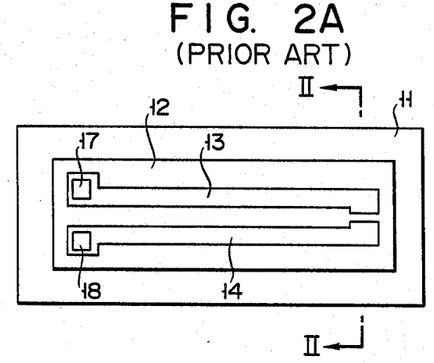
Figure 2B:
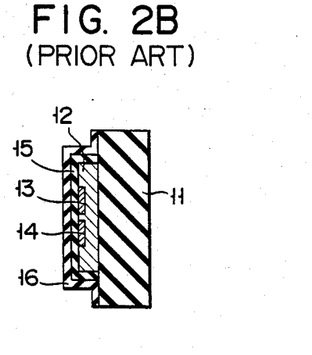

A sensor shown in FIGS. 2A and 2B has an SOS (Silicon On Sapphire) structure. In this sensor, p-type silicon island layer 12 is formed on sapphire substrate 11, and $n^+$-type source and drain regions 13 and 14 are formed thereon. Silicon oxide film 15 and silicon nitride film 16, respectively serving as a gate insulative film and a protective film, are formed on the surface of the silicon layer 12. In the sensor of this type, a gate portion of the FET is constituted by the source and drain regions, a channel region therebetween, and the insulative film on one side of silicon layer 12. Part of the insulative film is selectively etched on the other side of source and drain regions 13 and 14, and metal films 17 and 18 are formed as contact layers on the etched portion.

In the chemical sensor of the SOS structure, all the manufacturing processes can be performed in a planar process, allowing mass-production. When a plurality of elements are formed and each has a multistructure, element isolation is complete. However, since silicon layer 12 epitaxially grown on sapphire substrate 11 is thin (e.g., 1 $\mu$m or less), the wiring resistance of source and drain regions 13 and 14 becomes high, thus impairing the sensitivity of the sensor.

When the SOS substrate is used, it is necessary to dope Al from the sapphire layer. Further, the SOS substrate is inferior to bulk silicon in terms of crystallinity. The necessary Al doping and the poor crystallinity result in various problems such as low hole mobility and short lifetime. In addition, the SOS substrate is every expensive due to the use of a sapphire layer. Still further, the crystal defect will likely to increase when the substrate is heat-treated, because of the difference in thermal expansion coefficient between silicon and sapphire.

Figure 3:
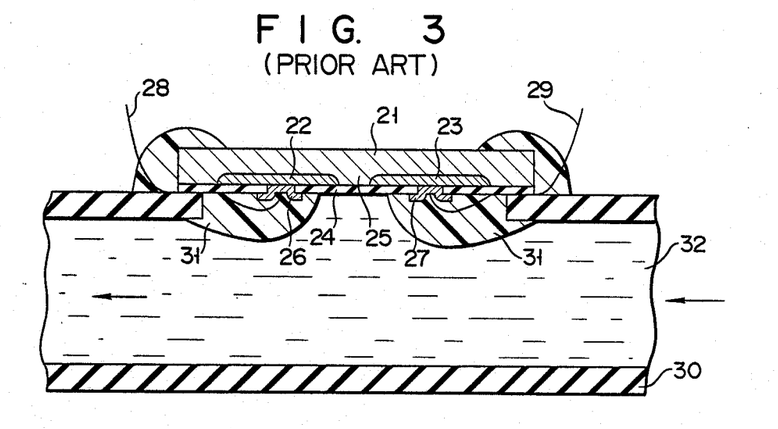
FIG. 3 is a sectional view schematically showing another conventional ISFET.

In a sensor shown in FIG. 3, $n^+$-type source and drain regions 22 and 23 are formed on a major surface of p-type silicon substrate 21, and insulative film 24 (e.g., a silicon nitride film or silicon oxide film) which serves as a gate insulative film and a protective film is also formed thereon. A portion between source and drain regions 22 and 23 serves as channel region 25. A gate portion of the FET is constituted by source and drain regions 22 and 23, channel region 25, and insulative film 24. Portions of insulative film 24 corresponding to source and drain regions 22 and 23 are selectively etched, and metal films 26 and 27 connected to source and drain regions 22 and 23 are deposited on the etched portions. Metal films 26 and 27 are also connected to lead wires 28 and 29. The chemical sensor with this structure is adhered to measurement tube 30, which is partially notched, by resin 31 so as to cover the connecting portions of metal films 26 and 27 and lead wires 28 and 29. The gate portion is dipped in solution 32 in tube 30 for measurement.

The chemical sensor of this structure can be manufactured by a planar process and is suitable for massproduction. However, lead wires 28 and 29 may become disconnected or peeled from metal films 26 and 27 in hardening the resin during the manufacturing process. In addition, when this sensor is used, resin 31 which is present at the same side as the detection surface is also dipped in solution 32 and expands, thus impairing its insulative property.

It would be difficult to form many sensor elements on the same substrate, without avoiding mutual interference among the elements.

In the above three types of sensors, after the passivation film is formed, it must be partially etched so as to form source and drain contact holes. Therefore, a material which is hard to be etched cannot be used as the passivation film. Although a silicon nitride film used as the passivation film can be easily etched by a reactive ion etching method or the like, it does not always have satisfactory passivation characteristics and ion selectivity. To achieve these qualities, an $Al_2O_3$ or $Ta_2O_5$ film is preferably used. However, since these films are hard to etch, contact portions thereof must be masked. In this case, an electron beam deposition method or a sputtering method which allows a low-temperature treatment is used, but traps may be produced in an interface between the substrate and the insulative film and the resultant films have poor characteristics. Although films formed by a CVD method have good characteristics, an appropriate masking material cannot be found because of high-temperature treatment in the CVD method.

SUMMARY OF THE INVENTION

It is an object of the present invention to provide a semiconductor sensor which can be manufactured by a planar process suitable for mass-production.

It is another object of the present invention to provide a method of manufacturing a semiconductor device suitable for mass-production.

According to the present invention, there is provided a semiconductor sensor comprising a first semiconductor substrate of a first conductivity type having one surface and an opposite surface, a second semiconductor substrate of the first conductivity type having one surface and an opposite surface, the one surface thereof being placed in contact with that of said first semiconductor substrate and said first and second semiconductor substrates being directly bonded together, a sensor region formed in one of said first and second semiconductor substrates, and a first insulative layer formed on at least said sensor region.

Furthermore, according to the present invention, there is provided a method of manufacturing a semiconductor sensor, comprising the steps of flattening, by polishing, one surfaces of first and second semiconductor substrates of a first conductivity type, each having one surface and an opposite surface, placing the one surfaces of said first and second semiconductor substrates in contact with each other and heating said first and second semiconductor substrates at a temperature of not less than 200° C. so as to bond them together, forming sensor elements having sensing sections in at least one of said first and second semiconductor substrates, coating at least said sensing sections of said sensor elements with an insulative layer, and cutting the bonded substrates into individual sensors.

DETAILED DESCRIPTION OF THE PREFERRED EMBODIMENTS

Figure 4:
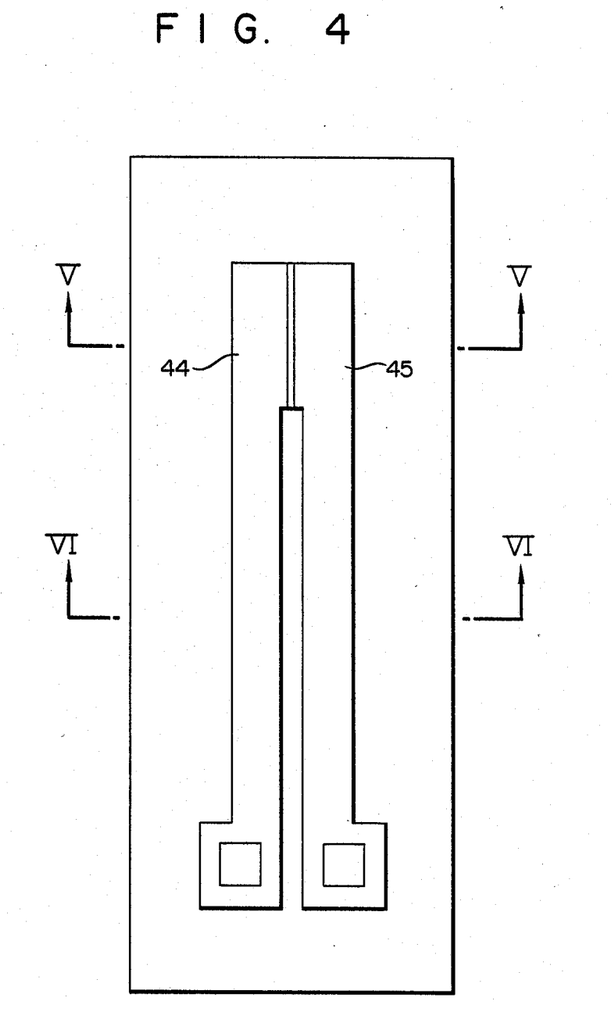
FIG. 4 is a plan view schematically showing an ISFET according to an embodiment of the present invention.
Figure 5:
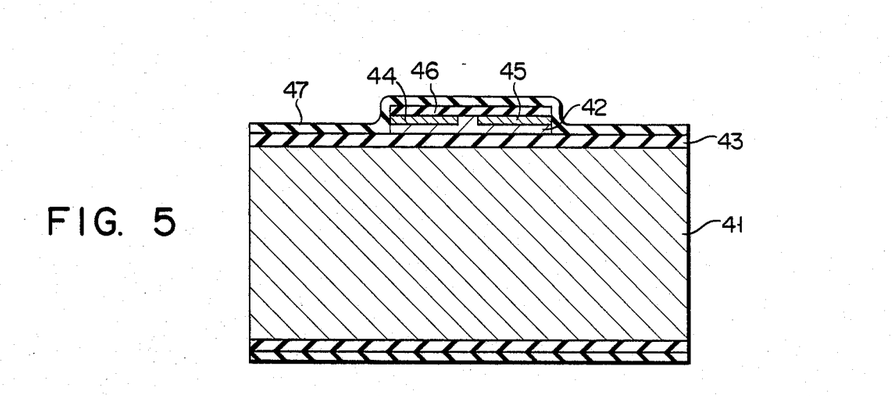
FIGS. 5 and 6 are sectional views taken along lines V—V and VI—VI of FIG. 4, respectively.
Figure 6:
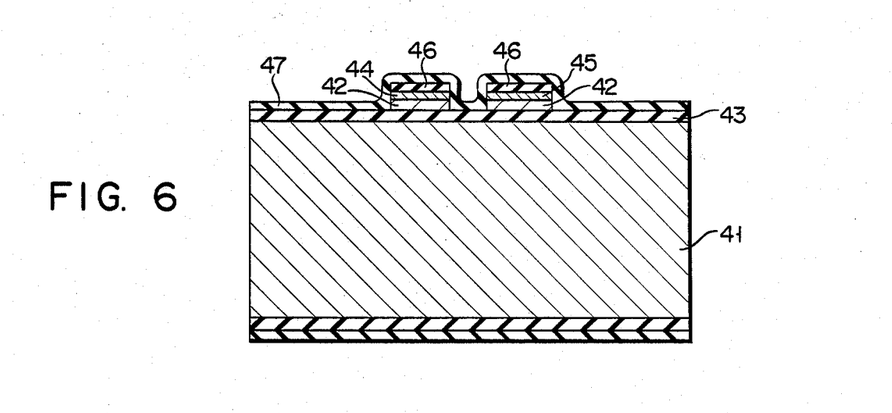

FIG. 4 is a plan view of an ISFET (ion selective field effect transistor) sensor according to an embodiment of the present invention. The ISFET sensor has a structure in which second Si substrate 42 is bonded to the upper surface of first Si substrate 41 through $SiO_2$ layer 43, as shown in FIGS. 5 and 6. Si substrate 42 is selectively formed on the central surface portion of Si substrate 41. Source and drain regions 44 and 45 are formed on the upper surface of Si substrate 42. A gate oxide film, $SiO_2$ film 46, is formed on the upper surface of Si substrate 42. $Si_3N_4$ film 47 as a passivation film is formed on the entire upper surface of the bonded structure of Si substrates 41 and 42.

With this structure, the elements formed on Si substrate 42 are completely surrounded by $SiO_2$ film 43 and $Si_3N_4$ film 47, and can be completely passivated.

The method of manufacturing the ISFET sensor shown in FIGS. 4 and 6 will be described with reference to FIGS. 7A to 7D.

Figure 7A:
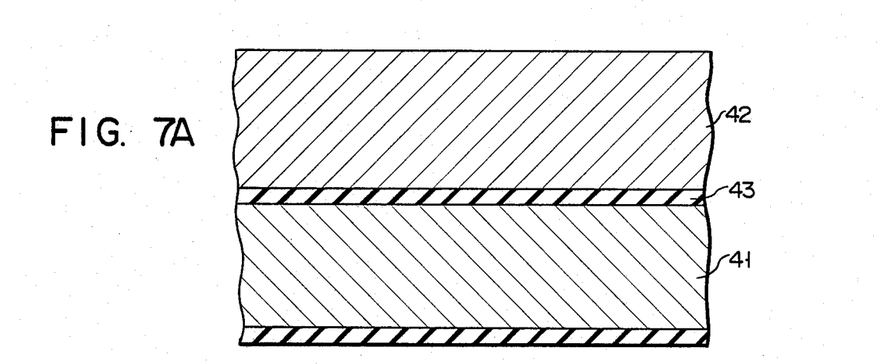
FIGS. 7A to 7D are sectional views showing steps in the manufacture of the ISFET shown in FIGS. 4 to 6.

P-type silicon wafers each having a diameter of 3 inches, a resistivity of 10 $\Omega$.cm, a thickness of 400 $\mu$m, a boron concentration of $10^{15}/cm^3$, and (100) crystal orientation, are prepared as first and second substrates 41 and 42, and the surfaces thereof to be bonded together are polished to obtain a surface roughness of 500 Å or less, and preferably 50 Å or less. These wafers are washed in a normal process using an organic solvent, a hydrogen peroxide+sulfuric acid, aqua regia boil, a hydrofluoric acid solution, or the like, and water as needed. Thereafter, silicon wafers 41 and 42 are oxidized in a high-temperature steam atmosphere, thus forming 1 $\mu$m thick oxide films 43 on their surfaces. Thereafter, silicon wafers 41 and 42 are washed with a hydrogen peroxide+sulfuric acid and aqua regia boil and water, and are then washed with deionized water for several minutes, thus performing the desired surface treatment. Thereafter, the surfaces of the wafers to be bonded are placed in contact with each other and are heat-treated in an electric furnace at a temperature of about 1,100° C. for 2 hours, thus bonding the wafers together. Any unnecessary oxide film 43 is then removed, as shown in FIG. 7A.

Figure 7B:
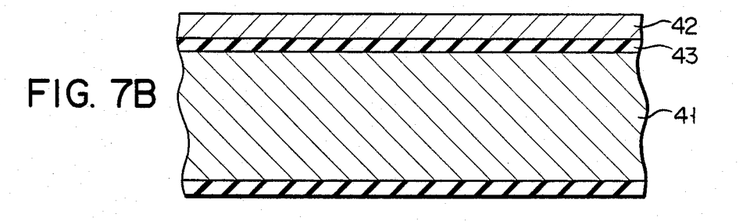

Upper Si wafer 42 is polished to obtain a thickness of 30 $\mu$m and, and is then mirror-polished, as shown in FIG. 7B. In this way, Si wafer 42 is formed as a thin Si substrate.

Figure 7C:
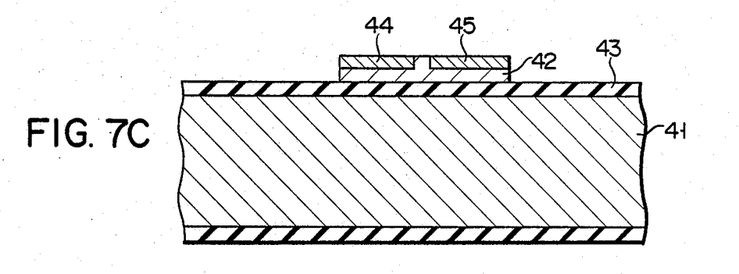

As shown in FIG. 7C, an impurity is selectively ion-implanted and diffused in Si wafer 42 to form source and drain regions 44 and 45. At the same time, a gate portion having a gate width of 400 μm and a gate length of 20 μm is formed. In this process, a plurality of FET elements are formed on substrates 41 and 42 so as to be separated each other. With this structure, since element isolation between the source and drain regions excluding the gate portion is complete, no channel stopper is required. Thereafter, the part of Si substrate 42 other than the element portion is etched, thus exposing SiO$_2$ film 43, as shown in FIG. 7C.

Figure 7D:
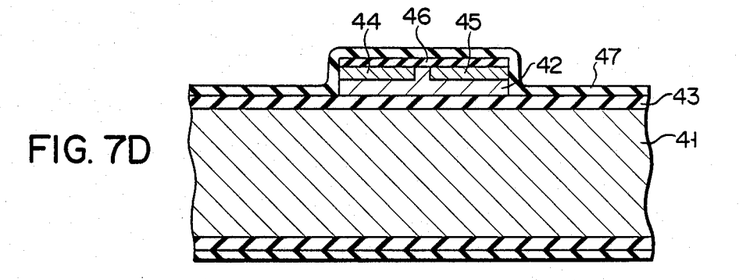

As shown in FIG. 7D, Si substrate 42 is then oxidized to form 500 Å thick gate oxide film 46. Thereafter, 800 Å thick Si$_3$N$_4$ film 47 is deposited on the overall surface of the structure by a CVD method. Portions of films 47 and 46 corresponding to contact forming portions are selectively etched and contact pads (not shown) are deposited thereon. The obtained structure is then cut into individual sensors with a known dicing method.

The thus produced ISFET as an H+ ion sensor exhibited selectivity of about 50 mV/PH like a conventional sensor, and no insulation breakdown was found over a long period of use.

With the method described above, an ISFET in which the element portion is completely passivated can be manufactured in a normal semiconductor manufacturing process, in which a large number of elements are formed on a single wafer, and are cut into devices by dicing. Furthermore, an Si substrate can be used in place of an SOS substrate. For this reason, the mass-production of these ISFETs is enabled, thus reducing their manufacturing cost.

In addition to the above advantages, an Si layer on the element forming side is sufficiently thick. For example, when a 3-inch standard wafer is used, the Si layer can have a thickness of 450 μm. With this structure, deep impurity diffusion is allowed, and resistance of wiring extending to the contact layers can be reduced. In contrast to this, in the SOS structure, since the Si layer is an epitaxially grown film, its thickness is limited (e.g., 20 μm or less).

When the SOS substrate is used, it is necessary to dope Al from the sapphire layer. Further, the SOS substrate is inferior to bulk silicon in terms of crystallinity. The necessary Al doping and the poor crystallinity result in various problems such as low hole mobility and short lifetime. In addition, the SOS substrate is very expensive due to the use of a sapphire layer. Still further, the crystal defect will likely to increase when the substrate is heat-treated, because of the difference in thermal expansion coefficient between silicon and sapphire.

Figure 8:
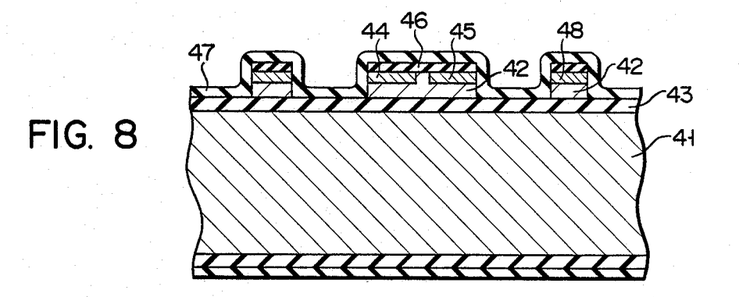
FIG. 8 is a sectional view schematically showing a modification of the ISFET shown in FIGS. 4 to 6.

The present invention is not limited to the above embodiment. For example, the number of elements which are formed on a single chip is not limited to one but can be 2 or more. In this case, element isolation is complete, and a channel stopper is not required, thus allowing the manufacture of a multistructure element. In addition, when part of the Si substrate is left to form diffusion resistance layer 48, as shown in FIG. 8, a sensor provided with a heater can be obtained. In this device shown in FIG. 8, sufficiently thick Si layer can be used so that sufficient current can be obtained and the heater characteristics can be improved. The passivation film is not limited to an Si$_3$N$_4$ film but can be an insulative film (e.g., SiO$_2$, SiN, Al$_2$O$_3$, or the like). Furthermore, an insulative wafer can be used instead of the Si wafer if it can be directly bonded to the Si substrate on the element forming side. In this case, since the wafer itself is an insulator, an SiO$_2$ film between the wafer and the Si substrate can be omitted.

An ISFET sensor according to another embodiment of the present invention will be described with reference to FIGS. 9 to 16.

Figure 9:
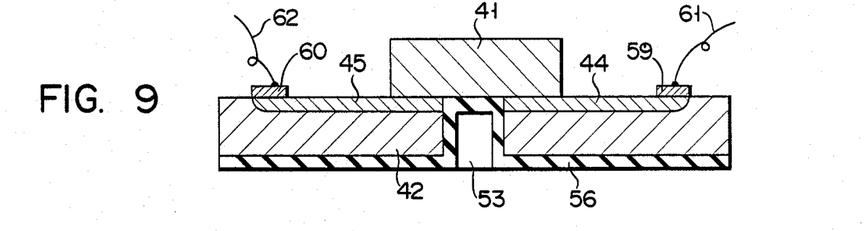
FIGS. 9 and 11 are sectional views schematically showing ISFETs according to another embodiment of the present invention.
Figure 10:
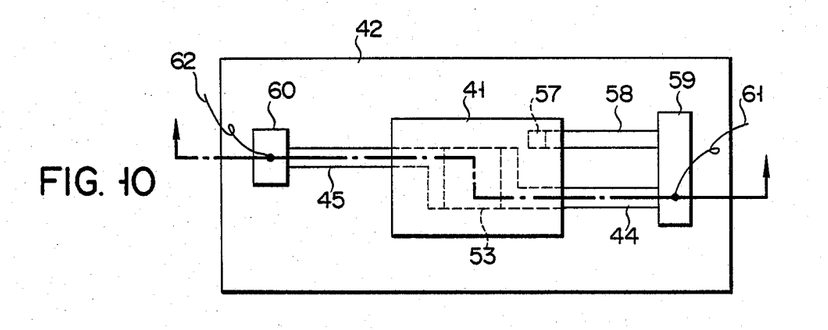
FIGS. 10 and 12 are plan views showing the ISFET of FIGS. 9 and 11.

In the ISFET shown in FIGS. 9 and 10, 2.5 mm×2.5 mm first p-type silicon substrate 41 having a thickness of 0.3 mm, and 4.5 mm×3 mm second p-type silicon substrate 42 having a thickness of 200 μm are directly bonded together in the same manner as in the above embodiment. 1 mm×20 mm through hole 53 is formed at the central portion of silicon substrate 42. Thus, second substrate 42 is bonded to first substrate 41 at the portion surrounding through hole 53. N+-type diffusion layers 44 and 45, serving as source and drain regions whose one end portions extend to through hole 53 and are electrically and are mechanically coupled to first silicon substrate 41, are formed on the surface of second silicon substrate 42 bonded to substrate 41. An impurity concentration of n+-type diffusion layers 44 and 45 is about 10$^{18}$/cm$^3$. The other end portions of diffusion layers 44 and 45 extend to regions of substrate 42 on which no substrate 41 is bonded.

Figure 12:
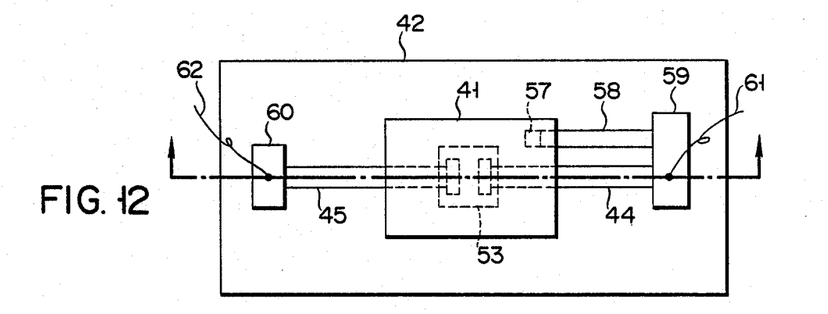

Insulative film 56, serving as a gate insulative film and a protective film, is formed on the surface of substrate 42 opposite to the bonding surface, the inner wall of through hole 53, and the surface of substrate 41 exposed in hole 53. P+-type diffusion layer 57 acting as a ground portion is formed on the bonding surface of substrate 41, and p+-type diffusion layer 58 corresponding thereto is formed on the bonding surface side of substrate 42 (FIG. 12). Layers 57 and 58 are connected together and have an impurity concentration of about 10$^{18}$/cm$^3$. Furthermore, metal film 59 connected to n+-type diffusion layer (source region) 44 and metal film 60 connected to n+-type diffusion layer (drain region) 45 are formed on the surface of substrate 42. Lead wires 61 and 62 are connected to metal films 59 and 60, respectively.

In the semiconductor sensor of this type, a region of substrate 41 between n+-type diffusion regions 44 and 45 is defined as a channel region having a channel length of 20 μm and a channel width of 1,000 μm, and insulative film 56 is formed thereon, thus constituting a gate portion of the FET in the deepest portion of through hole 53. The surface of the sensor on which insulative film 56 is formed serves as the detection surface, and is dipped in a solution. The connecting portions between n+-type diffusion layers 44 and 45 (i.e., the source and drain regions) and lead wires 61 and 62 are formed on the surface opposite to the detection surface.

Since the semiconductor sensor of this embodiment can be mounted along a tube wall, it can provide high mechanical strength or will not obstruct the flowpath of a solution in a measurement tube, unlike the conventional semiconductor sensor shown in FIGS. 1A and 1B. For example, when the sensor is mounted as a part of a tube, since only the detection surface is dipped in the solution, the source and drain connecting portions need not be covered with a resin, unlike the conventional semiconductor sensor shown in FIG. 3. Therefore, poor insulation due to expansion of the resin will not occur.

The semiconductor sensor shown in FIGS. 9 and 10 is manufactured in the following manner.

A p-type silicon wafer is cut and mirror-polished to prepare first silicon substrate 41 in the same manner as in the above embodiment. An oxide film is formed on the bonding surface of substrate 41, and is partially etched by a photoetching method. P+-type diffusion layer 57 acting as a ground portion is formed by impurity diffusion, and the oxide film is then removed. Meanwhile, a p-type silicon wafer is cut and mirrorpolished to prepare second silicon substrate 42 in the same manner as above. An n+-type diffusion layer acting as the source and drain regions and p+-type diffusion layer 58 as the ground portion are sequentially formed on substrate 42 through the same oxide film forming, photoetching, and impurity diffusion processes as for substrate 41. In this case, the n+-type diffusion layers can be formed separately from each other or as one layer. The central portion of substrate 42 is then selectively etched to form through hole 53. Thereafter, n+-type diffusion layers 44 and 45 are formed so that their one end portions extend to the inner wall of through hole 53. The bonding surfaces of first and second substrates 41 and 42 are washed with water to provide a hydrophilic property, are placed in tight contact with each other, and are heat-treated in air at a temperature of 1,000° C. for 2 hours, thus bonding them together.

The bonded structure is washed with a hydrofluoric acid based etching solution to remove the oxide film formed on the surfaces thereof. Insulative film 56 is formed on the surface of the structure, and a resist pattern is then formed on the detection surface. Insulative film 56 is then selectively removed, using the resist pattern as a mask. As a result, as shown in FIG. 9, insulative film 56 is left only on the detection surface. Film 56 can be a silicon oxide film or silicon nitride film, or can be a two-layered structure of the silicon oxide film with the silicon nitride film formed thereon. In the latter case, for example, a 500 Å thick silicon oxide film is formed on substrate 42 in $O_2$ atmosphere containing $O_2$ or HCl at a temperature of 1,100° C., and a 1,000 Å thick silicon nitride film is then formed thereon by a reduced-pressure CVD method, thus preparing the two-layered insulative film. Next, Cr and Au films are sequentially deposited on the entire surface of the structure, and are then patterned to form metal films 59 and 60 of the connecting portion. Lead wires 61 and 62 are then connected to films 59 and 60 by a wire bonding method or the like.

Various methods for bonding silicon substrates have been known. For example, two silicon substrates can be bonded using an organic or a glass-based adhesive. However, since a relatively thick insulative layer is undesirably formed between two substrates, this method cannot be applied to the manufacture of the semiconductor sensor shown in FIG. 9. Alternatively, an $SiO_2$ layer containing Na and the like is formed on the surface of one substrate, and the two substrates are bonded by applying a high voltage through this layer. However, this method cannot be adopted in the sensor in FIG. 9 for the same reason as above.

In another method, one substrate in which Na and the like is diffused is placed in contact with another, and high voltage is applied thereto to bond them together. In this method, however, since the resistance of the source and drain regions varies due to the $Na^+$ ion diffusion, this method cannot be adopted in the sensor of FIG. 9.

The direct bonding method adopted in this embodiment is free from the above drawbacks. Since two substrates can be bonded to provide a pressure resistance of 100 kg/cm$^2$, the sensor of this embodiment can be used in the measurement of a compressed solution.

Output characteristics with respect to a change in pH were measured using the semiconductor sensor of this embodiment and a buffer solution, as a solution to be measured. In this measurement, a saturated calomel electrode (SEC) was used as a reference electrode, and a current between the source and drain was fed back to the reference electrode by a source follower circuit so as to keep it constant. With the sensor of this embodiment good output characteristics were obtained (i.e., a change $\Delta VG$ in gate potential was 50 mV/pH at pH 1 to 12).

The same test was conducted for the semiconductor sensor shown in FIGS. 9 and 10 and the conventional sensor shown in FIG. 3. The sensors were mounted on measurement tubes, and pressure resistance and long-span reliability were compared. The results are as follows. Pertaining to pressure resistance, in the semiconductor sensor shown in FIG. 3, current leakage occurred at a gauge pressure of about 1.5 kg/cm$^2$, and the sensor became disabled. In contrast to this, element characteristics of the sensor of this embodiment were not changed when the measurement was conducted at the gauge pressure of 2 to 10 kg/cm$^2$. When the sensors were kept in a pH 6.8 solution for a long period of time, the output from the conventional sensor became unstable after about 800 hours and further measurement was impossible. After 970 hours had passed, the conventional sensor was completely disabled. In contrast to this, the semiconductor sensor shown in FIGS. 9 and 10 operated stably, even after 2,000 hours.

The structure of the semiconductor sensor according to the second embodiment of the present invention is not limited to that shown in FIGS. 9 and 10, but can be modified as follows.

Figure 11:
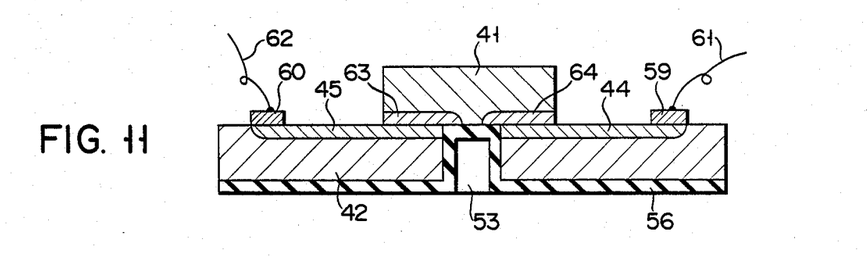

In a semiconductor sensor shown in FIGS. 11 and 12, n+-type diffusion layers 63 and 64, to be connected to n+-type diffusion layers 44 and 45 formed on second silicon substrate 42, are formed on the bonding surface of first silicon substrate 41. With this structure, the source region is defined by n+-type diffusion layers 44 and 63, and the drain region by n+-type diffusion layers 45 and 64. In the manufacture of this sensor, the step of forming n+-type diffusion layers 63 and 64 on the surface of first silicon substrate 41 is added to the method of manufacturing the sensor shown in FIGS. 9 and 10.

This structure can provide the same effects as the sensor shown in FIGS. 9 and 10 with the following difference. In the former sensor, the channel length is determined by a size of the through hole but in the latter sensor, it is determined by the photoetching method upon formation of n+-type diffusion layer 63. Therefore, either of the structures can be selected, taking the steps in their manufacture and controllability of the channel length into consideration.

In the above descriptions, insulative film 56 is formed only on the detection surface of the semiconductor sensor, as shown in FIGS. 9 and 10. However, the present invention is not limited to this. For example, the insulative film can have numerous variations, as shown in FIGS. 13 to 16. The sensors shown in FIGS. 13 and 14 have no n+-type diffusion layer on first silicon substrate 41, and the sensors shown in FIGS. 15 and 16 have the n+-type diffusion layer formed on first silicon substrate 41.

Figure 13:
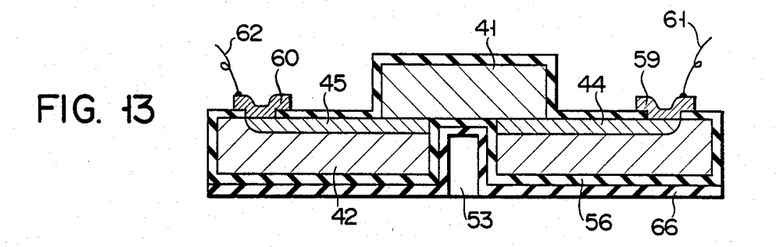
FIGS. 13 to 16 are sectional views showing modifications of an ISFET according to another embodiment of the present invention.
Figure 14:
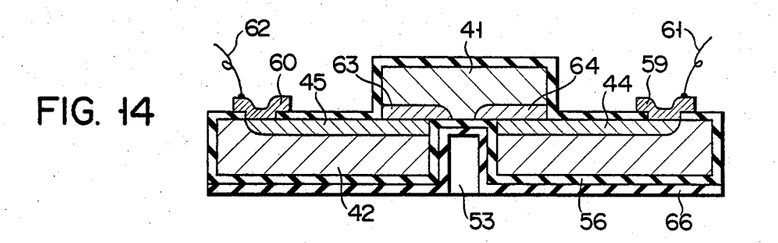
Figure 15:
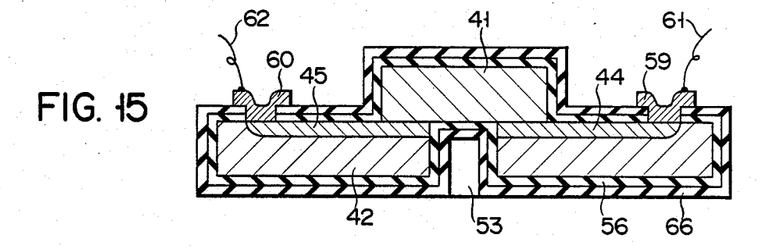
Figure 16:
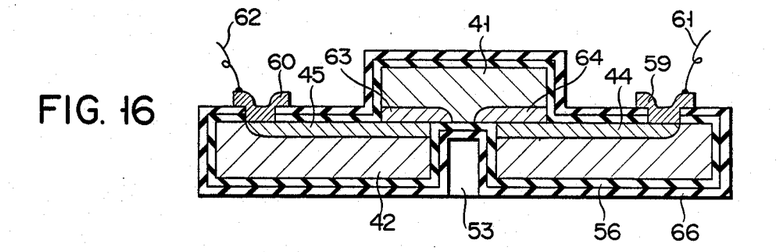

In the semiconductor sensor shown in FIGS. 13 and 14, thermal oxide film 56 is formed on the entire surface of substrate 41, and silicon nitride film 66 is then formed only on the detection surface. In the semiconductor sensor shown in FIGS. 15 and 16, thermal oxide film 56 and silicon nitride film 66 are sequentially formed on the entire surface of first and second silicon substrates 41 and 42. Note that in both the structures, metal films 59 and 60 of the connecting portions are formed in such a manner that portions of the insulative film corresponding to the metal film forming portions are selectively etched, and Cr and Au films are deposited thereon and are patterned thereafter.

Although $p^+$-type diffusion layer 57 is formed as a ground portion on substrate 41 (FIGS. 10 and 12), since first and second substrates 41 and 42 are directly bonded together, $p^+$-type diffusion layer 57 on the surface of substrate 41 is not always needed. More specifically, $p^+$-type diffusion layer 58 can be formed only on substrate 42, so as to obtain ohmic contact with metal film 59, and need only be connected to $n^+$-type diffusion layer (i.e., source region) 44.

In the above-mentioned test, only a pH (hydrogen ion concentration) was measured. However, the semiconductor sensor of the present invention is not limited to this, and can be applied to the measurement of other specific ions.

An ISFET sensor according to another embodiment of the present invention will be described with reference to FIG. 17.

Figure 17:
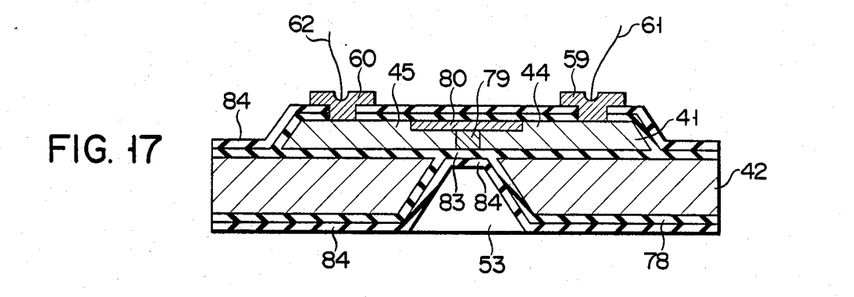
FIG. 17 is a sectional view schematically showing an ISFET according to another embodiment of the present invention.

In the ISFET sensor shown in FIG. 17, first and second Si substrates 41 and 42 are bonded together through silicon oxide film 43 in the same manner as in the sensor shown in FIG. 5, and unlike the sensor shown in FIG. 9. Source and drain regions 44 and 45 are formed on first Si substrate 41, and are separated by channel region 79 and channel stopper 80. In addition, metal films 59 and 60 as contact layers, which are connected to the source and drain regions, are formed on substrate 41.

The method of manufacturing the ISFET sensor shown in FIG. 17 will be described with reference to FIGS. 18A to 18F. After first and second Si wafers or substrates 41 and 42 are bonded together through silicon oxide film 43 in the same manner as shown in FIG. 7A, any unnecessary oxide film is removed from the bonded structure, thus preparing the structure shown in FIG. 18A.

Figure 18A:
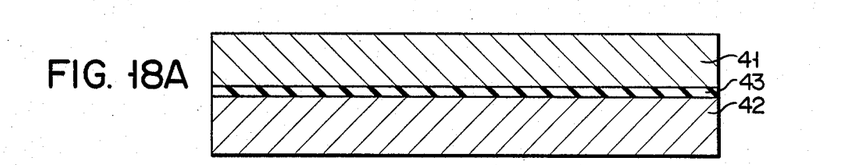
FIGS. 18A to 18F are sectional views showing the steps in the manufacture of the ISFET shown in FIG. 17.
Figure 18B:
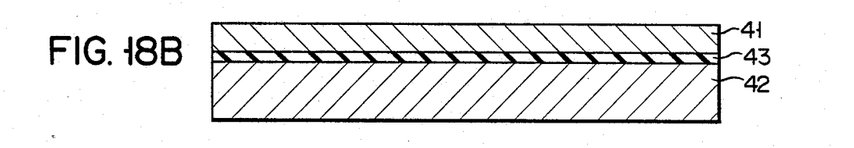
Figure 18C:
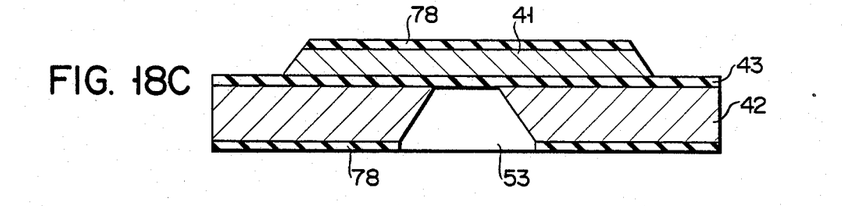

First Si substrate 41 is lapped from the surface opposite to the bonding surface to obtain a thickness of 10 $\mu$m, and is then mirror-polished. Oxide films 78 acting as etching masks are formed on the surfaces opposite to the bonding surfaces of first and second substrates 41 and 42. Thereafter, the part of substrate 41 and the exposed surface of substrate 42 are etched until oxide film 43 on the bonding surface is exposed, using EPW (a solution mixture of ethylene diamine-pyrocatechol-water) as an anisotropic etchant, thus forming groove 53. When the above etchant is used, etching progresses along the (111) surface, and the etching surface is inclined. In this case, an opening of groove 53 at the bonding surface side is designed to have a square shape with a 300 $\mu$m side.

Figure 18D:
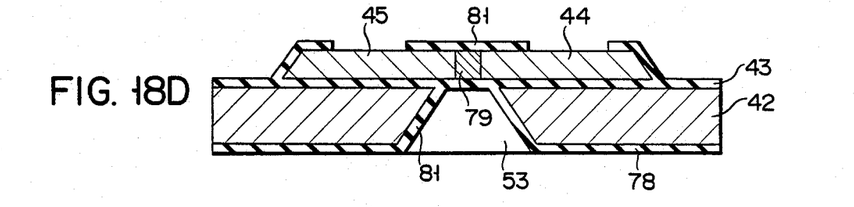
Figure 18E:
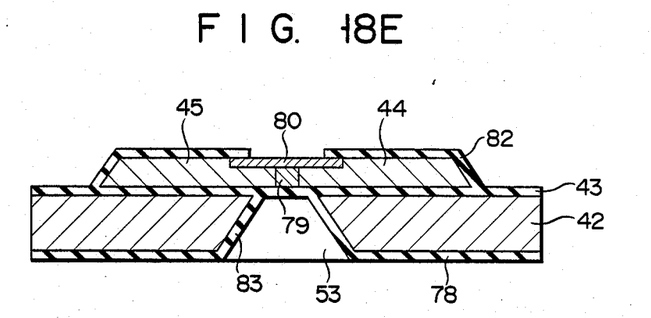

Subsequently, oxide film 81 serving as a diffusion mask is formed on the part of substrate 41 and the exposed surface of substrate 42. Phosphorus is then diffused from an opening of oxide film 81 formed on the surface of substrate 41 to the bonding surface, thus forming $n^+$-type source and drain regions 44 and 45, separated from each other. A region between source and drain regions 44 and 45 serves as channel region 79. Channel region 79 and the portions of source and drain regions 44 and 45 are formed to be exposed in groove 53 at the bonding surface side of substrate 41, as shown in FIG. 18D. Then, oxide film 82 serving as a diffusion mask is formed on the part of substate 41 and the exposed surface of substrate 42. Boron is then diffused into substrate 42 to form $p^+$-type channel stopper region 80 in the surface of substrate 41 opposite to the bonding surface, as shown in FIG. 18E.

Figure 18F:
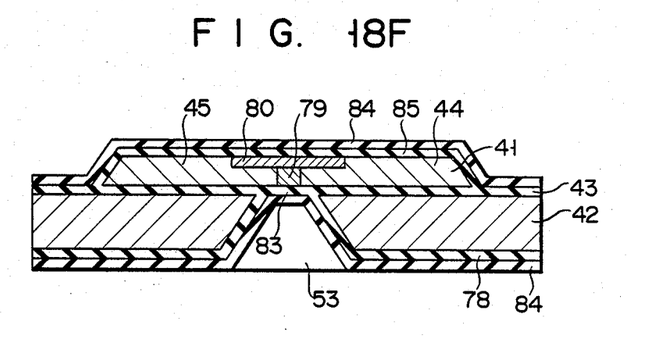

After oxide film 82 is removed from substrate 41, and the parts of oxide film 78 formed on the gate portion and the inner surface of groove 53 are selectively removed, 800 Å thick oxide film 85 and 800 Å thick gate oxide film 83 are formed on the structure. Next, 800 Å thick silicon nitride film 84 serving as a passivation film is deposited on the entire surface of film 85 by an LPCVD method, as shown in FIG. 18F. Silicon nitride film 84 and part of oxide film 85 are selectively etched to form contact holes in the surface of substrate 41, opposite the bonding surface, and corresponding to source and drain regions 44 and 45. Subsequently, Cr and Au films are sequentially deposited on the overall surface of substrate 41 and are patterned, thus forming contact pads 59 and 60. Thereafter, individual elements are cut from the wafer using a dicer, and lead wires 61 and 62 are connected to pads 59 and 60, thus completing the chemical sensor shown in FIG. 17.

Figure 19:
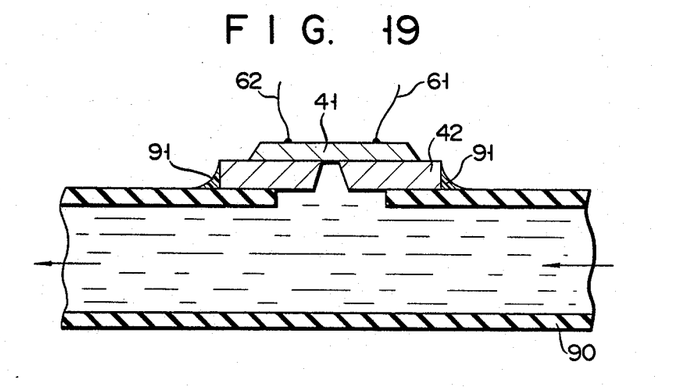
FIG. 19 is a sectional view showing the ISFET of FIG. 17 in use.

As shown in FIG. 19, the chemical sensor is mounted on a notched portion of flow cell 90 and sealed with resin 91, thus being suitable for measuring specific ion concentration in the solution flowing through flow cell 90.

In this chemical sensor, after first and second silicon substrates 41 and 42 are bonded together through oxide film 43, all other purposes can be performed by a planar process. In addition, since first silicon substrate 41, on which elements are formed, has a dielectric isolation structure covered with an insulative film, this method is suitable for mass-production.

Unlike the SOS chemical sensor shown in FIG. 3, since first silicon substrate 41, in which source and drain regions 44 and 45 are formed, can be thick (in the above embodiment, 10 $\mu$m after lapping), sensitivity of the sensor according to the invention will not be degraded due to an increase in wiring resistance. In the sensor according to the invention, the substrate silicon has a good crystallization and has not the problem because the substrates have same thermal expansion coefficients. In addition, since the elements are dielectrically isolated, they can have multistructure, and a temperature detection element, an amplification or operational element or circuit can be easily formed in addition to the chemical sensor. Since an epitaxial growth apparatus and expensive sapphire substrates are unnecessary, manufacturing costs can be reduced.

The gate and contact portions are formed on opposite surfaces and the contact portion need not be placed in contact with a solution, thus preventing poor insulation due to expansion of resin. Similarly, since the gate and contact portions are formed on the opposite surfaces, a passivation film (e.g., $Al_2O_3$ or $Ta_2O_5$), which has good passivation characteristics and ion selectivity and is hard to etch, can be formed in place of silicon nitride film 84. In the contact portion, since a passivation film having good etching properties need only be formed, selectivity can be improved even more.

Unlike a conventional sensor in which gate and contact portions are on the same surface, the gate portion of the sensor of this embodiment does not require resin molding at all and resin molding can be performed on the entire surface of the contact portion. Therefore, a given space need not be provided in order to expose the gate portion. When the detection element has multistructure or when a temperature detection element, an amplification or operational element or circuit, or the like is formed, elements can be formed at minimum distances. In this way, the method of this embodiment can cope with higher integration.

Furthermore, since the sensor of this embodiment can be mounted along the wall surface of the flow cell, as shown in FIG. 19, a flow-path resistance can be reduced.

In a test where the sensor was mounted as shown in FIG. 19 and pH response characteristics were measured by a source follower circuit using a saturated calomel electrode as a reference electrode, linear response (i.e., about 50 mV/pH at pH 2 to 11) was obtained, and drift over time was satisfactory.

The chemical sensor of the present invention can have selectivity for other ions, in addition to hydrogen ions (pH), when various selective ion sensitive films are formed on the gate portion. In addition, since the selective ion sensitive film is formed in the groove, a bonding strength of the selective ion sensitive film is improved. More specifically, since a selective ion sensitive film often comprises an organic material, it is generally difficult to bond the film to the surface of an inorganic material element, and the film tends to swell in an aqueous solution. For this reason, when the selective ion sensitive film is applied to a chemical sensor of planar structure, it is easily peeled therefrom, thereby limiting the durability of the element. In contrast to this, when the selective ion sensitive film is formed in the groove, as in the chemical sensor of the present invention, the groove is placed in contact with the selective ion sensitive film over a large contact area. When the selective ion sensitive film swells, a pressure force acts on the film towards the substrate facing the groove, and easy peeling of the selective film is prevented thereby.

Figure 20:
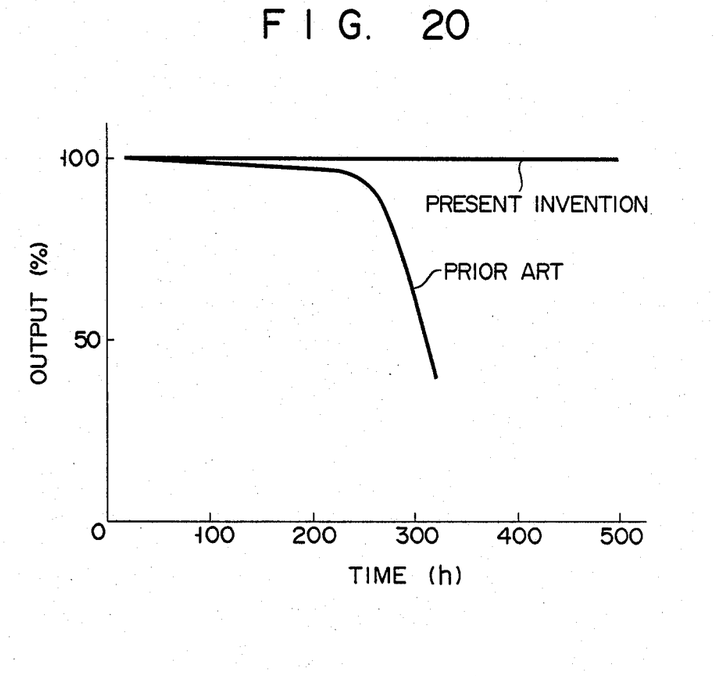
FIG. 20 is a graph comparing durabilities of the ISFET shown in FIG. 17 and a conventional ISFET.

In a test of a chemical sensor using a selective ion sensitive film, a K$^+$ sensor using a Valinomycin containing PVC film, an Na$^+$ sensor using a crown ether containing PVC film, and a Cl$^-$ sensor using an ammonium salt containing PVC film were produced. When characteristics of these sensors were examined, linear response (i.e., about 50 mV/pX) was provided within the range of $10^{-1}$ to $10^{-5}$ mol/l of K$^+$ and Na$^+$, and within the range of $10^{-1}$ to $10^{-4}$ mol/l of Cl$^-$. A change in output over time was examined for the Na$^+$ sensor of the present invention and a Na$^+$ sensor having a conventional planar structure by dipping them into an aqueous solution. As shown in FIG. 20, the structure of the present invention provided a stable output over a long period of time, and the bonding strength of the selective film was improved, thus prolonging sensor life.

Figure 21:
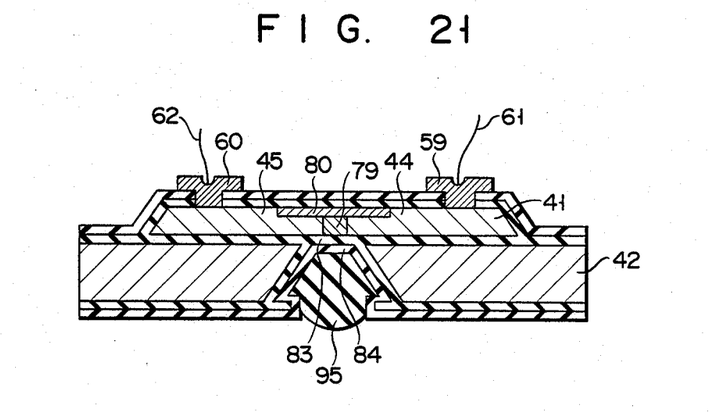
FIG. 21 is a sectional view schematically showing a modification of the ISFET shown in FIG. 17.

If insulative films formed on the surface of second silicon substrate 42 opposite to the bonding surface (e.g., an oxide film serving as an etching mask, and a silicon nitride film as a passivation film) are formed to overhang groove 53, as shown in FIG. 21, the bonding strength of selective ion sensitive film 95 formed in groove 53 can be improved.

In addition to the above selective ion sensitive films, the sensor of the present invention can be used with an enzyme selective sensitive film for glucose, urea, penicillin, or the like, or a microorganism selective sensitive film.

Furthermore, if the outer surface of the groove is covered with a gas permeable film and an electrolytic solution or a gel is filled in the groove, the sensor of the present invention can serve as a $CO_2$ gas sensor.

According to the present invention as described above, a chemical sensor can be manufactured by a planar process, is suitable for mass-production, is not adversely influenced by wiring resistance or resin swelling, can use a desired passivation film, and has a good selectivity, wide application range, and long life.

What is claimed is:

1. A semiconductor sensor comprising:
   a first semiconductor substrate of a first conductivity type having one surface and an opposite surface;
   a second semiconductor substrate of the first conductivity type having one surface and an opposite surface, the one surface thereof being placed in contact with that of said first semiconductor substrate and said first and second semiconductor substrates being directly bonded together;
   a sensor region formed in one of said first and second semiconductor substrates;
   a first insulative layer formed on at least said sensor region which is made of one material selected from the group consisting of silicon nitride, silicon oxide, aluminum oxide, tantalum oxide, titanium oxide, zirconium oxide, niobium oxide, and hafnium oxide, and which further comprises a second insulative layer formed on said first insulative layer, and wherein said sensor region has a field effect transistor structure for detecting an ion concentration.

2. A sensor according to claim 1, wherein said first and second semiconductor substrates are silicon substrates.

3. A sensor according to claim 1, further comprising:
   a silicon oxide layer formed on at least one of the one surfaces of said first and second semiconductor substrates,
   said first and second semiconductor substrates being bonded together through said silicon oxide layer.

4. A sensor according to claim 1, wherein said second insulative layer is made of a material different from that of said first insulative layer, and which is selected from the group consisting of silicon nitride, silicon oxide, aluminum oxide, tantalum oxide, titanium oxide, zirconium oxide, niobium oxide, and hafnium oxide.

5. A semiconductor sensor comprising:
   a first semiconductor substrate of a first conductivity type having one surface and an opposite surface;
   a second semiconductor substrate of the first conductivity type having one surface and an opposite surface and a through hole extending from the one surface to the opposite surface thereof, the one surface being placed in contact with that of said first semiconductor substrate and said first and second semiconductor substrates being directly bonded together;
   source and drain regions formed by diffusing an impurity of a second conductivity type in the one surface of said second semiconductor substrate, separated by said through hole, and extending along the one surface of said second semiconductor substrate which is in contact with said first semiconductor substrate; and
   a first insulative layer formed on the opposite surface of said second semiconductor substrate, an inner surface of said through hole, and the one surface of said first semiconductor substrate exposed in said through hole.

6. A sensor according to claim 5, wherein said first and second semiconductor substrates are silicon substrates.

7. A sensor according to claim 5, wherein said first insulative layer is made of one material selected from the group consisting of silicon nitride, silicon oxide, aluminum oxide, tantalum oxide, titanium oxide, zirconium oxide, niobium oxide, and hafnium oxide.

8. A sensor according to claim 7, further comprising a second insulative layer formed on said first insulative layer.

9. A sensor according to claim 8, wherein said second layer is made of a material different from that of said first insulative layer, and which is selected from the group consisting of silicon nitride, silicon oxide, aluminum oxide, tantalum oxide, titanium oxide, zirconium oxide, niobium oxide, and hafnium oxide.

10. A sensor according to claim 5, further comprising:
source and drain regions formed by diffusing an impurity of a second conductivity type, separated from each other on the one surface of said first semiconductor substrate exposed in said through hole, and extending along the one surface of said first semiconductor substrate.

11. A sensor according to claim 5, further comprising:
contacts formed on the one surface of said second semiconductor substrate and connected to said source and drain regions, respectively.

12. A semiconductor sensor comprising:
a first semiconductor substrate of a first conductivity type having one surface and an opposite surface;
a second semiconductor substrate on said opposite surface having one surface and an opposite surface, and a through hole extending from the one surface to the opposite surface;
a first insulative layer formed on at least the one surfaces of said first and second semiconductor substrates, the one surfaces being in contact with each other, and said first and second semiconductor substrates being bonded together through said first insulative layer;
source and drain region formed on said first semiconductor substrate by diffusing an impurity of the second conductivity type, and separated from each other on the one surface of said first semiconductor substrate exposed in said through hole; and
a second insulative layer formed on the opposite surface of said second semiconductor substrate, an inner surface of said through hole, and the one surface of said first semiconductor substrate exposed in said through hole.

13. A sensor according to claim 12, wherein said first and second semiconductor substrates are silicon substrates.

14. A sensor according to claim 12, wherein said first insulative layer is made of one material selected from the group consisting of silicon nitride, silicon oxide, aluminum oxide, tantalum oxide, titanium oxide, zirconium oxide, niobium oxide, and hafnium oxide.

15. A sensor according to claim 14, further comprising a second insulative layer formed on said first insulative layer.

16. A sensor according to claim 15, wherein said second layer is made of a material different from that of said first insulative layer, and which is selected from the group consisting of silicon nitride, silicon oxide, aluminum oxide, tantalum oxide, titanium oxide, zirconium oxide, niobium oxide, and hafnium oxide.

17. A sensor according to claim 12, further comprising:
contacts formed on the opposite surface of said first semiconductor substrate and connected to said source and drain regions, respectively.

18. A sensor according to claim 12, further comprising:
a film arranged in said through hole, wherein said film is an ion sensitive film, an enzyme or microorganism selective sensitive film, or a gas permeable film.

19. A sensor according to claim 12, further comprising:
a channel stopper formed in the opposite surface of said first semiconductor substrate.

* * * * *